United States Patent [19]

Bradford

[11] Patent Number: Plant 6,981

[45] **Date of Patent: * Aug. 15, 1989**

[54] NECTARINE TREE (SPARKLING JUNE)

[76] Inventor: Norman G. Bradford, 11875 Savana Rd., Le Grand, Calif. 95333

[ * ] Notice: The portion of the term of this patent subsequent to Nov. 15, 2003 has been disclaimed.

[21] Appl. No.: 702,911

[22] Filed: Feb. 19, 1985

[51] Int. Cl.[4] ..... A01H 5/00

[52] U.S. Cl. ..... Plt./41

[58] Field of Search ..... Plt. 41

*Primary Examiner*—Robert E. Bagwill

*Attorney, Agent, or Firm*—Worrel & Worrel

[57] ABSTRACT

A new and distinct variety of Nectarine Tree which is somewhat similar to the Early Sun Grand Nectarine Tree, U.S. Plant Pat. No. 1,420, and the Red Diamond Nectarine Tree, U.S. Plant Pat. No. 3,165, but which is distinguished therefrom and characterized as to novelty by producing fruit which is ripe for commercial harvesting 18 days earlier than the Red Diamond Nectarine Tree and 14 days earlier than the Early Sun Grand Nectarine Tree, and which has excellent handling and storage characteristics.

1 Drawing Sheet

BACKGROUND OF THE NEW VARIETY

The present invention relates to a new and distinct variety of freestone nectarine tree denominated varietally as "Sparkling June", and more particularly to a new and distinct variety broadly characterized by a medium sized hardy, productive and regular bearing tree, the fruit of which ripens around fourteen days earlier than the Early Sun Grand Nectarine Tree (U.S. Plant Pat. No. 1,420) with which it is closely related, but from which it is distinguished as to novelty by bearing fruit which has a fuller red color at picking time as compared to other known early varieties, is of excellent firmness, and has excellent shelf life and shipping qualities. Also, the fruit has a noteworthy taste and is less deeply sutured resulting in a more pleasing shape.

For years the applicant has endeavored to produce new and distinct varieties of fruit trees in an effort to upgrade the quality of his fruit tree products. In these labors to produce these new and distinct varieties, the applicant has, as a regular practice, selected parent trees having desirable characteristics, cross-pollinated the subject parents, and thereafter studied the progeny produced to ascertain whether any new and distinct varieties are present. The instant variety of Nectarine Tree, "Sparkling June" is a product of the aforementioned procedure.

ORIGIN AND ASEXUAL REPRODUCTION OF THE NEW VARIETY

The seedling of the present variety was the offspring of an open-pollination of a second generation seedling from a Red Diamond Nectarine tree seed parent (U.S. Plant Pat. No. 3,165), cross-pollinated with an Early Sun Grand Nectarine Tree pollen parent (U.S. Plant Pat. No. 1,420). This procedure was first carried out in 1977 by the applicant at his ranch, which is located at 9766 E. Mariposa Way, LeGrand, Calif.; in the County of Merced. The unique qualities of the subject variety were first recognized in 1981, and the applicant thereafter asexually reproduced the subject variety by budding and grafting. It has been subsequently determined that the progeny produced from these asexual reproductions are identical to those of the original seedling.

SUMMARY OF THE NEW VARIETY

The "Sparkling June" Nectarine Tree is characterized by many of the desired features of the "Red Diamond" Nectarine tree, (U.S. Plant Pat. No. 3,165) and the "Early Sun Grand" Nectarine Tree, (U.S. Plant Pat. No. 1,420). The new variety resembles the Red Diamond Nectarine Tree in producing fruit which resembles closely the color and fruit size produced by the Red Diamond Nectarine tree. The subject variety also produces fruit which resembles in size, and stone characteristic the fruit produced by the Early Sun Grand Nectarine Tree. The new variety is, clearly distinguishable, however, from the fruit produced by the Red Diamond Nectarine Tree and the Early Grand Nectarine Tree inasmuch as it ripens for harvesting 18 days earlier than the Red Diamond Nectarine Tree, and 14 days earlier than the Early Sun Grand Nectarine Tree and has a much richer red color.

BRIEF DESCRIPTION OF THE DRAWING

The accompanying drawing is a color photograph of four mature nectarines showing their external coloration sufficiently mature for harvesting and shipment, two mature nectarines halved transversely of the suture plane to illustrate the flesh coloration, several characteristic leaves showing their dorsal surface coloration, and two stones, all of the subject variety.

DETAILED DESCRIPTION

Referring now more specifically to the pomological characteristics of this new and distinct variety of nectarine tree, the following has been observed under the ecological conditions prevailing near Le Grand, Merced County (San Joaquin Valley), Calif. All color plate identifications are by reference to the Inter-Society Color Council—National Bureau of Standards. Common Color names are also used occasionally.

TREE

General: Medium in size, hardy, vigorous and dense, spreading and vase formed depending upon pruning practices. Productive and regular bearing.

Trunk: Of medium diameter, surface texture — medium shaggy. Numerous tan lenticles are present. Size —

Lenticels — average size approximately 3/16" in length [4.762 mm.]

*Branches.*—Medium in size and surface texture; second year and older growth is brown in color [58. m Br], newer growth appears red brown on dorsal side [43. m. r Br] and green [136. m. y G] on ventral side.

Leaves:

*Size.*—Average length 4½"; [114.3 mm]; average width 1⅝"[41.275 mm]

*Form.*—Elliptical.

*Base.*—Acute.

*Apex.*—Accuminate.

*Margin.*—Crenate.

*Veins.*—Pinnately, net veined.

*Petiole.*—Size — Medium — average length ½"; [12.7 mm]; medium thickness approximately 1/16 inch, [1.588 mm].

*Glands.*—Numbers — average two to four per leaf, mostly opposite. Reniform, green glands appear on the petiole at the base of the leaf. Color — Yellowish green [136. m. y G.]

*Stipules.*—Numbers — usually two per leaf, length — approximately ¼" in length [6.35 mm].

*Leaf buds.*—Form — pointed. Leaf Color — Dorsal Surface — Yellowish green [137. d. y G]; Leaf Color — Ventral Surface — Yellowish green [136. m. y G]; Petiole Color — Yellowish green [136 m. y. G].

Flowers:

*Buds.*—Hardy, medium in length and diameter, pointed, free, pubescent.

*Flowers.*—Generally — Large; Date of Bloom — medium bloom date as compared with other varieties. Pink in color. The color of the subject varieties flowers are not particularly distinctive.

FRUIT

Maturity when described: Fully ripe for commercial harvesting on June 28, 1984.

Size: Uniform, medium in size, axial diameter 2¼"[57.15 mm]. diameter transverse in the suture plane approximately 2¼ inches, [57.15 mm]

Form: Uniform, symmetrical; globose to slightly oblong.

Suture: Generally — inconspicuous line which extends from the base to beyond the apex. The suture appears as a slight depression beyond the pistil point.

Ventral surface: Slightly rounded, lipped toward the apex on both sides, lips are slightly unequal.

Cavity:

*Shape.*—Rounded with suture showing on one side depth — approximately ⅜ inch [9.525 mm]; Breadth — approximately ⅜ inch [9.525 mm]; Stem marking — are evident a few stem marks.

Base: Generally — symetrically truncate, the fruit sits on the base in a very upright position.

Apex: Rounded, with some slightly depressed.

*Pistil point.*—Mostly apical but a few oblique may be found. Size — very small approximately 3½ inches, [88.9 mm].

Stem: Medium in size; Length — approximately 5/16 inches, [7.938 mm]; width — approximately ⅛ inch, [3.175 mm].

Skin: Generally — thin, tough. Tendency to crack is slight (none observed in 1983 and 1984). Tenacious to flesh.

*Skin color.*—Approximately 95% of the surface of the fruit is a deep red color, [13. deep red], however, some yellow coloration can be detected in the stem cavity [86.1 Y].

Flesh:

*Color.*—Generally — The flesh is yellowish in color throughout, [86.1. Y.], however a tinge of red appears next to the skin on the ripest fruit; surface of pit cavity — pale yellow [86.1. Y]. A few yellowish colored fibers are evident [86.1 Y.].

*Texture.*—Extremely firm, very crisp.

*Fibers.*—Few, fine, tender.

*Ripens.*—Evenly.

*Flavor.*—Acid to sub-acid.

*Juice.*—Moderate.

*Aroma.*—Very slight.

*Amygdalin.*—Scarce.

*Eating quality.*—Very good.

STONE

Generally: Freestones

Form: Oval.

Base: Straight.

Apex:

*Shape.*—Acute; Sides — generally equal; curved on right.

Surface:

*Generally.*—A few regular furrows appear near the apex pitted from the base to a position slightly above center throughout.

Ridges: Present; the ridges appear jagged toward the apex.

Color of stone: orangish brown, [78. d. y Br].

Thickness of pit wall: approximately ¼ inch, [6.35 mm].

Tendency to split is slight.

Kernel: Oval in form, sweet, viable, width — approximately 7/16 inches, [11.112 mm]; length — approximately ⅝ inch, [15.875 mm], yellow pellicle, scant amygdalin.

Resistance to Insects and Disease: No unusual susceptibilities noted.

Use: Local market, long distance shipping. Excellent keeping quality and excellent shipping quality.

Although the new variety of nectarine tree possesses the described characteristics as a result of the growing conditions prevailing in LeGrand, Calif., in the central part of the San Joaquin Valley, it is to be understood that variations of the usual magnitude and characteristics incident to changes in growing conditions, fertilization, pruning and pest control are to be expected.

Having thus described and illustrated my new variety of Nectarine Tree, what I claim as new and desire to secure by Plant Letters Patent is:

1. A new and distinct variety of freestone nectarine tree, substantially as illustrated and described, which is somewhat similar to the Early Sun Grand Nectarine Tree (U.S. Plant Pat. No. 1,420), and the Red Diamond Nectarine Tree (U.S. Plant Pat. No. 3,165) from which it was derived as a progeny, but is distinguished therefrom by producing fruit which is ripe for commercial harvesting fourteen days earlier than Early Sun Grand Nectarine Tree, and 18 days earlier than the Sun Diamond Nectarine Tree, the variety having a good flavor, a fuller red color, and a more desirable, less deeply sutured shape, and is further characterized by its excellent firmness, shipping quality, and shelf life.

* * * * *

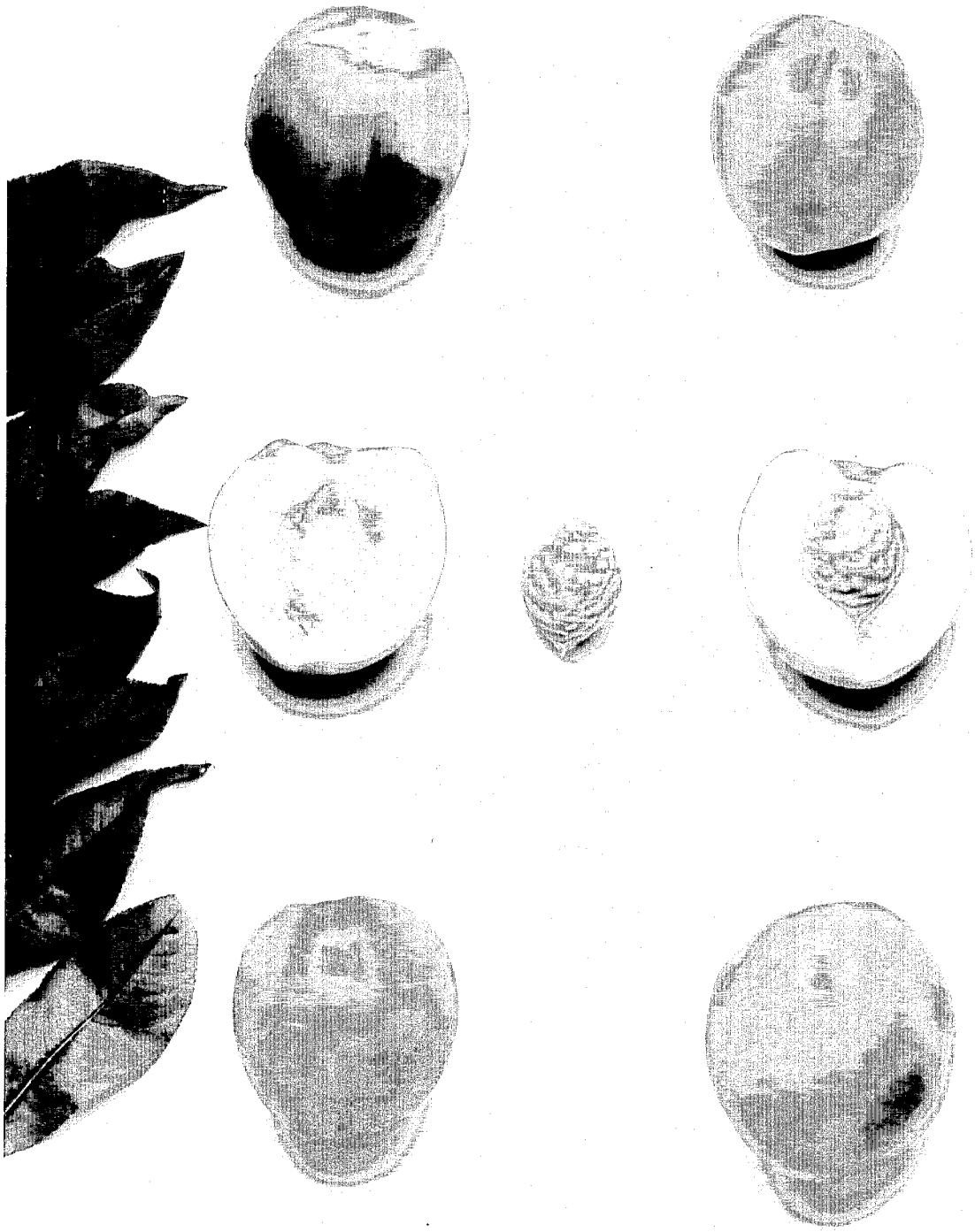

UNITED STATES PATENT AND TRADEMARK OFFICE

CERTIFICATE OF CORRECTION

PATENT NO. : PP6,981

DATED : August 15, 1989

INVENTOR(S) : Norman G. Bradford

It is certified that error appears in the above-identified patent and that said Letters Patent is hereby corrected as shown below:

On the title page:

In the title delete "NECTARINE TREE (SPARKLING JUNE)"
and insert --NECTARINE TREE "SPARKLING JUNE"--

Col. 3, line 43, delete "." and insert --,--

Col. 3, line 47 insert --an-- after the dash

Col. 3, line 56, delete "are evident a few stem marks." insert
--a few stem marks are evident.--

Signed and Sealed this

Seventeenth Day of July, 1990

*Attest:*

*Attesting Officer*

HARRY F. MANBECK, JR.

*Commissioner of Patents and Trademarks*